United States Patent [19]

Sheridan

[11] Patent Number: 4,949,858

[45] Date of Patent: Aug. 21, 1990

[54] SAMPLE BOTTLE AND CAP THEREFOR

[75] Inventor: Michael Sheridan, Old Bridge, N.J.

[73] Assignee: Ethylene Corp., Murray Hill, N.J.

[21] Appl. No.: 367,781

[22] Filed: Jun. 19, 1989

[51] Int. Cl.$^5$ .............................................. B65D 45/04
[52] U.S. Cl. ....................................... 215/330; 215/293
[58] Field of Search ................ 215/330, 293; 220/322, 220/324

[56] References Cited

U.S. PATENT DOCUMENTS 1,592,147  7/1926  Mletschnig ........................... 215/330
4,746,027  5/1988  Coker ................................... 215/293

Primary Examiner—Donald F. Norton
Attorney, Agent, or Firm—Charles E. Temko

[57] ABSTRACT

A sample collection container for use in receiving samples for analysis and testing of fluids from a sample valve forming part of a chemical process line. The container includes a closure element which selectively engages the sample valve during collection and provides means for protecting the user handling the sample container after disengagement from the sample valve from spillage. The container closure is selectively engageable by a cap element when disengaged from the sample valve, the cap element having an orificed end wall which may be selectively closed or provided with means supporting a penetrable membrane for hypodermic extraction of fluid.

7 Claims, 2 Drawing Sheets

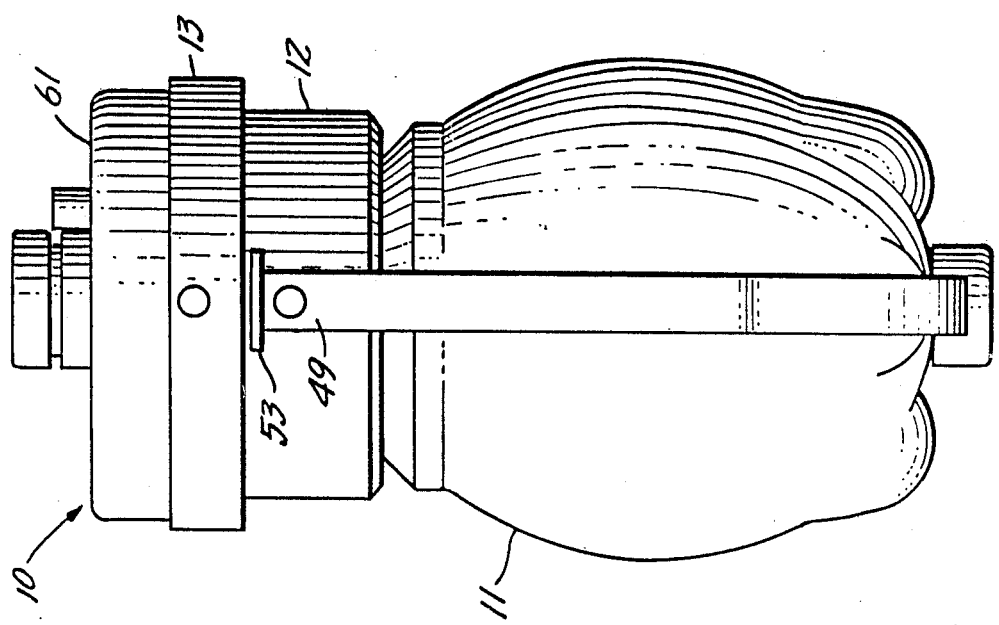
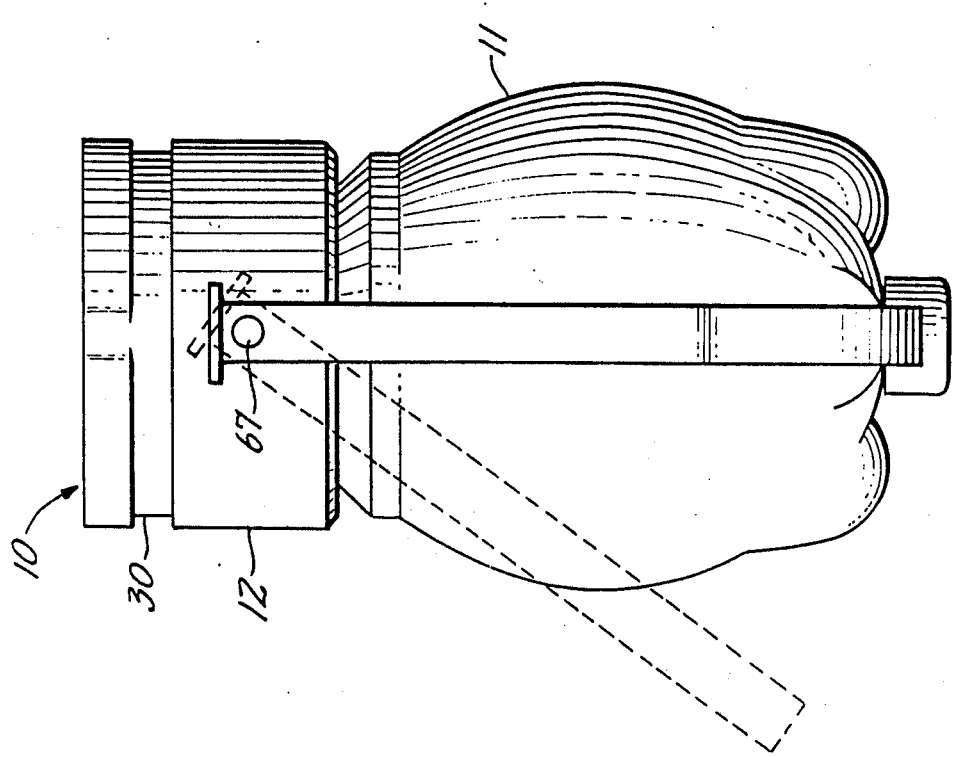

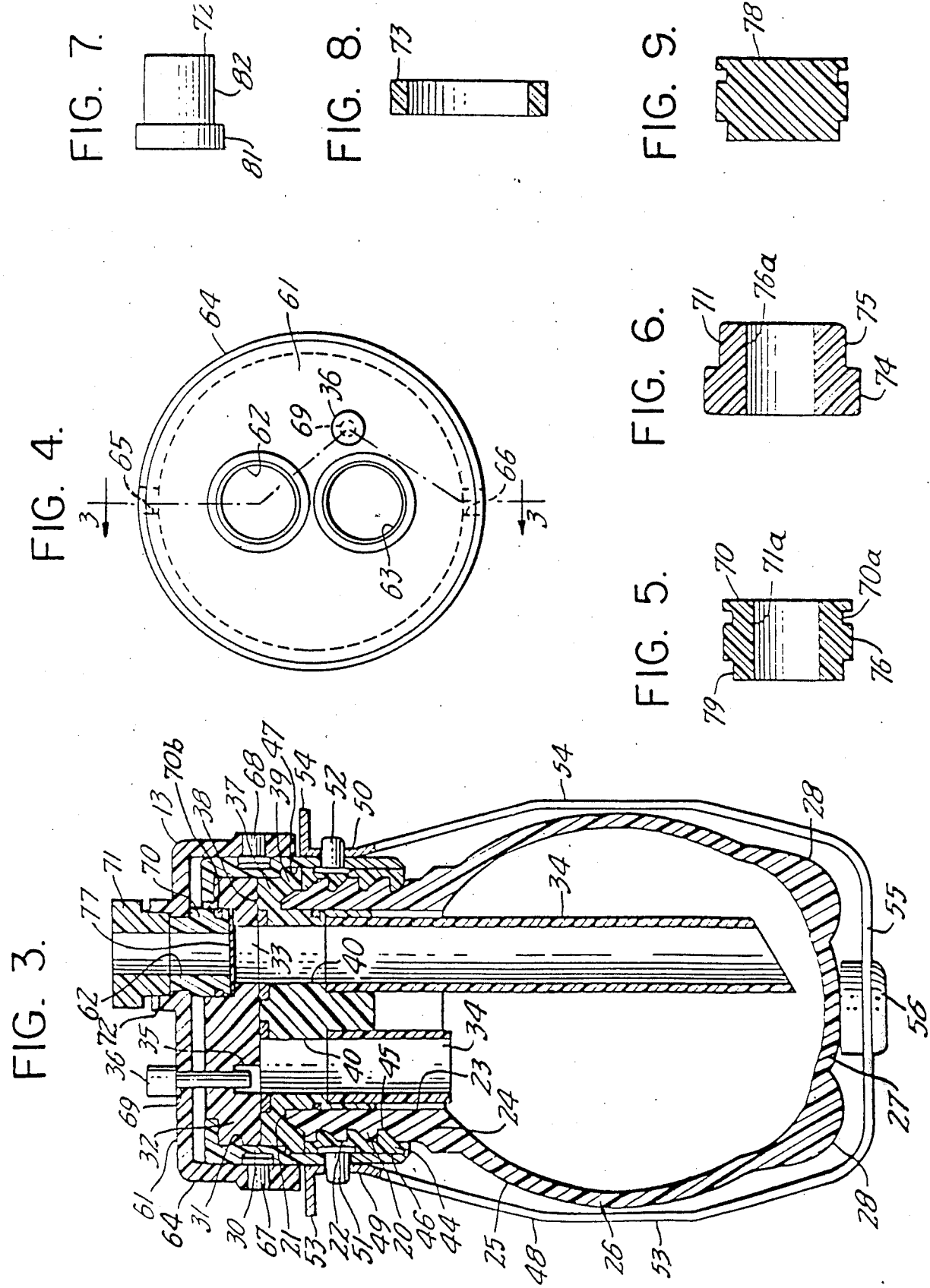

SAMPLE BOTTLE AND CAP THEREFOR

RELATED APPLICATION

Reference is made to co-pending application Ser. No. 267,984 filed Nov. 7, 1988, now U.S. Pat. No. 4,873,876 and entitled "Chemical Process Sampler," said application being assigned to the same assignee as the present application, and disclosing and claiming a related invention.

BACKGROUND OF THE INVENTION

This invention relates generally to the field of chemical processing, particularly processing of toxic volatile or otherwise dangerous substances, and more particularly to an improved process sampling system by means of which small quantities of substances to be examined may be removed from a reacting mass for analysis at convenient intervals during a processing cycle. Devices of this general type are known in the art, and the invention lies in specific constructional details which afford increased convenience with regard to the recycling of a tested sample, and, more importantly, increased safety to the technician or operator conducting the sampling operation.

The need for obtaining uncontaminated representative samples of chemical processing operations has been one of long-standing. The most common method employed involves the use of a so-called dip tube which is projected through or mounted within an orifice in the reactor vessel. Where the sample material is not particularly dangerous, this structure has proved adequate.

More sophisticated sampling devices include those sold under the trademark DOPAK. These devices include a means for connecting into the process line at a suitable point which means includes a valve to control flow to a sample container. Adjacent to the valve is a pair of hollow needles, both of which penetrate a self-sealing diaphragm or septum located beneath the threaded cap of the sample container. One needle feeds the sample, while the other needle exhausts air or other displaced fluid within the container. When the container is filled with the sample to desired volume, the container is disconnected from the needles without spillage.

Another type of sampling device is market under the trademark POSACON. This type of device is installed in line with a conduit, and includes a transversely extending needle valve which communicates with a selectively engageable piston injector which operates somewhat in the manner of a hypodermic syringe. The injector has means for closing the same against leakage before disconnecting from the valve body.

In both types of devices, above described, after examination and/or testing of the sample, there remains the problem of disposing of the unused portion thereof which may create environmental problems, particularly where the samples are corrosive, toxic, or otherwise dangerous.

In the above identified co-pending application there is disclosed a sample valve construction which provides for collection of a sample from a process line into a sample container and the disconnection and removal of the sample container from the valve for analysis of the contents. The sample container is removable only after it is placed in closed condition, and the user must open the closure in order to gain access to the collected sample, usually by unthreading the container from the closure element to prevent manipulation of the cover plate overlying the opening in the neck of the container. Once the required sample has been removed for analysis, the remainder of the sample can be returned to the process line, thereby simplifying disposal. In the case of samples obtained under pressure, substantially above atmospheric pressure, use is made of an optional safety enclosure through which visual observation of the collection of the sample may be made without risk to the technician.

In the above-described structure, however, it is possible for the technician to accidentally unthread the container or bottle from the engaged bottle closure while the latter is still engaged with the sample valve structure with the possibility of spillage of at least a part of the then collected sample. This might occur, for example, when the threaded engagement of the bottle is more easily dislodged than the bayonet engagement of the bottle closure with the sample valve structure. Another difficulty has been experienced in the case where it is desired to extract a part of the collected sample by means of a hypodermic syringe or the like through a self-sealing membrane without the need of uncovering the openings in the cover plate, this type of extraction being particularly desirable where the quantity of the required sample is relatively small, and the potential danger in handling the sample is significant.

SUMMARY OF THE INVENTION

Briefly stated, the present invention contemplates the provision of an improved sampling container or bottle and associated structure for use in conjunction with devices disclosed in the above-mentioned application, in which the engagement, disengagement and accessing of the contents of the container has been facilitated. To this end, means is provided for preventing the unthreading of the bottle from the bottle closure member while the bottle closure member is still engaged with bayonet means on the sample valve structure. Also provided is an improved cap structure adapted to overly the bottle closure member after disconnection from the sample valve structure which provides means for accessing the bottle contents through a cover plate either directly, or through an intervening membrane type closure.

BRIEF DESCRIPTION OF THE DRAWINGS

In the drawings, to which reference will be made in the specification, similar reference characters have been employed to designate corresponding parts throughout the several views.

FIG. 1 is a side elevational view of a sample container embodying the invention in disengaged condition relative to a sample valve structure.

FIG. 2 is a similar view in elevation showing the subsequent placement of a cap element overlying the container closure element.

FIG. 3 is a vertical longitudinal sectional view as seen from the plane 3—3 in FIG. 4.

FIG. 4 is a top plan view of a cap element forming part of the disclosed embodiment.

FIG. 5 is a longitudinal central sectional view of a cap tube forming a part of the disclosed embodiment.

FIG. 6 is a longitudinal central sectional view of a cap plug forming another part of the disclosed embodiment.

FIG. 7 is a side elevational view of a cap pin forming still another part of the embodiment.

FIG. 8 is a side elevational view of a cap bushing.

FIG. 9 is a longitudinal sectional view showing another form of the structure illustrated in FIG. 5.

DETAILED DESCRIPTION OF THE DISCLOSED EMBODIMENT

In accordance with the invention, the device, generally indicated by reference character 10, comprises broadly: a bottle element 11, a bottle closure element 12 and a cap element 13.

The bottle element 11 is preferably formed from molded polytetrafluoroethylene (PTFE), and resembles in configuration that illustrated in the above-mentioned co-pending application. It includes a threaded neck 20 defining an upper sealing periphery 21, an outer threaded surface 22, an inner cylindrical surface 23 and a lower reinforced area 24 located in an area of normally encountered greater stress. A main body 25 is bounded by a quasispherical side wall 26 and a curved lower wall 27 preferably provided with integrally molded projections 28 which provide a surface for standing the bottle upon a horizontal surface.

The bottle closure element 12, again, is generally similar to that disclosed in the mentioned application, and provides a bayonet type flange 30 and a recess 31 for a cover plate 32 having countersunk openings one of which is indicated by reference character 33 for fill tube 34 and vent tube 34A. Vent opening 35 is selectively closed by a small insertible pin 36. A bottle closure plate 37 includes an upper wall 38 and a cylindrical shank 39. Counterbores 40 communicate selectively with openings 33.

Beneath the plate 37 is a threaded member 44 having an internally threaded surface 45 and an outer cylindrical surface 46 which bears against an inner surface of the flange 30. A pivotally mounted strap 48 is interconnected at the free ends 49 and 50 to pins 51 and 52. The strap includes longitudinal segments 53 and 54 and a bottom segment 55 supporting a pressure pad 56 which engages a lower surface of the bottle. As best seen in FIGS. 1, 2 and 3, it will be apparent that when the strap is in longitudinally aligned relation, it prevents the unthreading of the bottle from the closure element 12. When either the cap element 13 is in position, or the closure element 12 is engaged with the valve structure as disclosed in the identified application, contact of the laterally extending segments 53 and 54 with either of these structures prevents lateral displacement of the strap, thus assuring that the bottle element 11 cannot be separately unthreaded, which is prevented by contact of a lower wall 27 with pad 56. When the bottle is removed from the valve structure, this can be accomplished only by disengaging the closure element 12 therefrom. As will more fully appear, when the cap element 13 is in position as shown in FIGS 2 and 3, a similar result obtains.

The cap element 13 serves to provide a safety cover for the device 10 when not engaged with the sample valve structure. It is most conveniently formed from molded polyvinylchloride, or materials possessing similar properties, and includes an end wall 61 having plural through bores 62 and 63, and a cylindrical side wall 64 terminating in an arcuate lower edge having oppositely disposed bores 65 and 66 which support bayonet pins 67 and 68 engaging flange 30. A venting bore 69 communicates with the vent opening 35. The cap element also includes a group of molded members which can be selectively engaged within one or more of the bores 62 and 63 depending upon the type of closure and function required. Certain of these members interconnect the sides of the openings in the cap element with bores in the cover plate 32, so that rotation of the cap element and cover plate with respect to the bottle closure element will permit alignment of the openings in each for communication therethrough. Other members are adapted to engage at least one of the through bores in the cap element from opposite sides thereof to determine an interstice which will support a penetrable membrane which will normally maintain the bottle element in closed condition, but which provides access to a hypodermic needle or similar device for the controlled extraction of small amounts of a collected sample. These parts include a cap tube 70 (FIG. 5), a cap plug 71 (FIG. 6), a cap pin 72 (FIG. 7), a cap bushing 73 (FIG. 8) and a second cap member 78 (FIG. 9).

The cap tube 70 is shown in position in FIG. 3, and includes a first cylindrical portion 76 which engages one of the through bores 62–63 in the end wall 61. It includes a first cylindrical portion 76 of relatively greater diameter, and a second cylindrical portion 79 of relatively smaller diameter. When positioned with the cap element as shown in FIG. 3, a groove 70A supports a sealing member 70b (not shown). The through bore 71 is of lesser diameter than the corresponding openings in the cover plate 32.

The cap plug 71 is also shown in position in FIG. 3, and is configured to cooperate with the cap tube 70. It includes a first cylindrical portion 74 and a second cylindrical portion 75 between which a through bore 76a extends. When in the position shown in FIG. 3, the members 70 and 32 define a planar interstice which positions a penetrable membrane or septum 77 to provide access to the needle of a syringe or the like (not shown). Where this facility is not required, the tube 70 may be replaced by an alternate solid member 78 (FIG. 9) which is identical, except for the omission of the through bore.

FIG. 7 illustrates a cap pin 72 which selectively replaces the cap plug 71 in a similar manner. It includes a first cylindrical flange portion 81 and second cylindrical portion 82, and may be used to seal the bores in the cap element. In such case, access to the bottle is made by rotating the cap element relative to the bottle closure element to permit removal of the cap element therefrom, at which time the openings in the closure element and the cover plate 32 will be aligned. Referring to FIG. 8, member 73 is shown in fused condition in FIG. 3, it being more conveniently molded as a separate member for subsequent assembly to the cap element 13.

From a detailed consideration of the above-described structure, it will be apparent that the safety provisions therein incorporated cannot be accidentally defeated, and, indeed, for the most part cannot be intentionally defeated. From the moment at which the sample bottle has been filled, the removal of the bottle from communication with sample valve structure cannot be accomplished by unthreading the bottle element. Rather, the closure element must be disengaged from its bayonet interconnection with the sample valve structure (not shown), which movement serves to disalign the openings in the closure element and the cover plate, thus providing initial protection.

Unless the technician has a specialized tool for the purpose, he cannot align the opening in the closure element with those in the cover plate without first engaging the cap element 13 upon the upper surface of the closure element. Relative rotation between the cap element and the closure element must then occur to align the openings in the closure element and the cover plate, wherein the plate 32 rotates relative to the plate 37 which movement will also align the openings in the cap element as well. Depending upon the mode of extraction of a sample, the cap element will have been provided either with fully plugged openings, or membrane supporting members which will permit access to the bottle by means of a hypodermic syringe needle or the like. If a small amount of the sample can be poured from the container, this is accomplished by passing the liquid through the above-described aligned openings, following which rotation of the cap element will close the sample container until such time as further operations are necessary. When it is desired to return the remainder of the sample to the process line, the operation is equally simple. The cap element is twisted to a position wherein the bayonet interconnection is disengaged and the cap removed, which readies the closure element for engagement with the sample valve structure in a manner described in the identified co-pending application. When the device has been disconnected after return of the contents, the strap element in the absence of the side wall 64 may then be pivoted as indicated in dashed lines in FIG. 1 to permit unthreading of the bottle element relative to the closure element for cleaning and/or replacement.

I wish it to be understood that I do not consider the invention to be limited to the precise details of structure shown and set forth in this specification, for obvious modifications will occur to those skilled in the art to which the invention pertains.

I claim:

1. Improved sample bottle structure for use in withdrawing samples from a sample valve structure comprising: a bottle element having an end wall and a bottle closure element; threaded means selectively interconnecting said bottle element to said bottle closure element, and pivotally mounted U-shaped strap means carried by said bottle closure element and selectively engaging said end wall of said bottle element in one pivotal position thereof to prevent the unthreading of said bottle element from said bottle closure element, and means selectively engaging said bottle closure element for preventing movement of said strap means from said one pivotal position.

2. Improved sample bottle structure in accordance with claim 1, said last mentioned means comprising: a cap element adapted to overly said bottle closure element in engaged condition therewith, said engagement serving to inhibit pivotal movement of said strap element out of contact with said bottle element.

3. Improved sample bottle structure in accordance with claim 2, further characterized in said cap element having a cylindrical side wall terminating in an arcuate edge surface, said strap element having laterally extending flanges thereon selectively engaging said edge surface to prevent pivotal movement.

4. Improved sample bottle structure in accordance with claim 3, further characterized in the provision of bayonet interconnecting means for maintaining said cap element upon said bottle closure element.

5. Improved sample bottle structure in accordance with claim 4, further characterized in said cap element including a transversely extending end wall having through openings therein, said bottle closure element having corresponding openings alignable therewith when said bayonet interconnecting means is in fully engaged condition.

6. The improved sample bottle structure in accordance with claim 5, further comprising selectively engageable plug means for closing said openings in said end wall.

7. Improved sample bottle structure in accordance with claim 5 further comprising a tubular element selectively engageable with at least one of said through openings in said bottle closure element in aligned spaced relation to define an interstice therebetween, and a penetrable resilient septum supported within said interstice.

* * * * *